United States Patent [19]

Pascoe

[11] Patent Number: 4,590,293

[45] Date of Patent: May 20, 1986

[54] PROCESS AND APPARATUS FOR FURTHER PROCESSING OF PRESSURIZED EXOTHERMIC REACTIONS

[75] Inventor: Ralph F. Pascoe, Marysville, Ohio

[73] Assignee: Ashland Oil, Inc., Russell, Ky.

[21] Appl. No.: 592,739

[22] Filed: Mar. 23, 1984

Related U.S. Application Data

[63] Continuation of Ser. No. 340,442, Jan. 18, 1982, abandoned.

[51] Int. Cl.$^4$ .................. C07C 67/38; C07C 51/14
[52] U.S. Cl. ........................... 560/233; 562/521; 260/544 A; 422/205
[58] Field of Search ................. 560/233; 562/521; 260/544 A

[56] References Cited

U.S. PATENT DOCUMENTS 3,052,698  9/1962  Friedman .................. 560/233

FOREIGN PATENT DOCUMENTS 46-35722  10/1971  Japan ..................... 560/233
1174209  12/1969  United Kingdom ............ 560/233
2082574   8/1980  United Kingdom ............ 518/704

OTHER PUBLICATIONS

Meissner, "Processes and Systems in Industrial Chemistry," pp. 89-93, 100-110 (1971).

*Primary Examiner*—Michael L. Shippen
*Attorney, Agent, or Firm*—Pollock, Vande Sande & Priddy

[57] ABSTRACT

An exothermic reaction's heat of a low-temperature reaction is used for further processing of the product mixture, for example, to separate the product from the reaction mixture.

19 Claims, 1 Drawing Figure

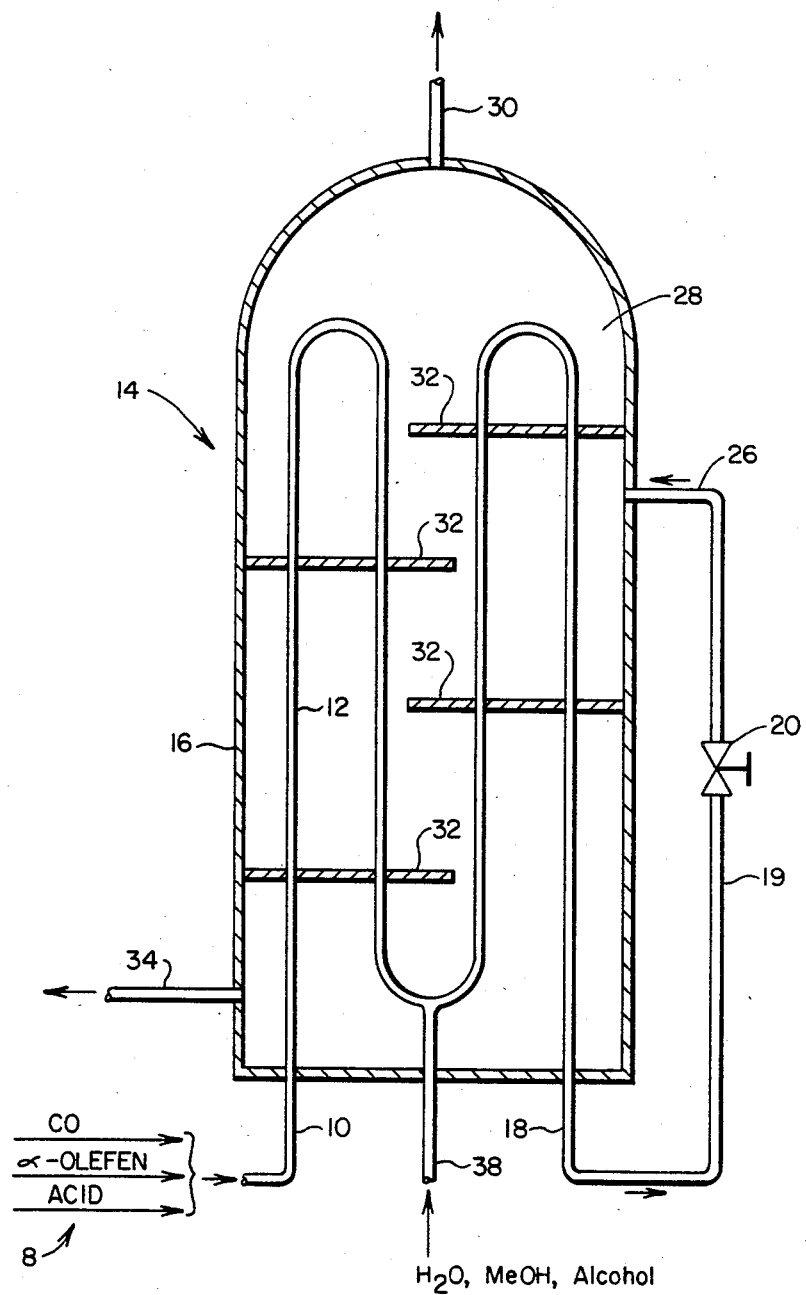

4,590,293

PROCESS AND APPARATUS FOR FURTHER PROCESSING OF PRESSURIZED EXOTHERMIC REACTIONS

This application is a continuation, of application Ser. No. 340,442, filed 1/18/82 now abandoned.

BACKGROUND OF THE INVENTION a. Field of the Invention

The invention relates to a process, e.g., carbonylation, and apparatus for further processing of exothermic chemical reactions occurring under pressure and at low temperatures (e.g., about 100° Centigrade).

b. Description of the Prior Art

The prior art describes apparatuses with heat exchangers which are suitable for high-temperature reactions, but not for low-temperature exothermic reactions. The general practice for low-temperature exothermic reactions is to cool low-temperature exothermic reactions with a cooling medium such as water and treat the heat as waste.

SUMMARY OF THE INVENTION

The continuous process employing the exothermic heat of reactions occurring at low temperatures below about 100° Centigrade and pressures up to 10,000 psia to heat the product mixture for subsequent processing stages comprises the following cycle of steps:

(a) reacting a mixture of reactants, e.g., $CO_2$, CO, HF, and propylene, at 2,000 psia and 80° C. under conditions whereby a predetermined amount of a product mixture, e.g., $CO_2$, CO, HF, isobutyryl fluoride and propylene, and exothermic heat forms, (b) adiabatically expanding the product mixture to below the temperature and pressure of the reaction conditions of step (a), e.g., 40 psia and 50° C., (c) heating the expanded product mixture of step (b) with the exothermic heat of reaction from a reaction mixture reacting in step (a) by passing the heat to the adiabatically expanded product mixture, and (d) transferring the heated product mixture of step (c) to the next processing step, e.g., distillation column, evaporator, etc. In another embodiment, the product mixture of step (a) is reacted with another reactant, e.g., $H_2O$ or methanol, to form a final product mixture, e.g., one comprised of isobutyric acid and/or methyl isobutyrate (step e) and then performing steps (b), (c), and (d) upon the final product mixture of step (e). In another embodiment, steps (b) and (c) result in the separation of one or more components from the product mixture, e.g., $CO_2$, CO or HF, are separated from the isobutyryl fluoride. An apparatus to perform the process is also disclosed herein.

BRIEF DESCRIPTION OF THE DRAWING

The drawing schematical depicts an apparatus for conducting the process described herein.

DESCRIPTION OF THE INVENTION a. General Description of the Process

The continuous process described herein employs the exothermic heat of a reaction occurring at pressures up to 10,000 psia, such as carbonylation reactions, and low temperatures up to 100° C., to heat the product mixture for subsequent processing steps such as distillation, evaporative separation, etc. The process comprises:

(a) reacting a mixture of reactants, under pressure and a low temperature under conditions whereby a predetermined amount of a product mixture and exothermic heat forms, (b) adiabatically expanding the product mixture of step (a) to below the temperature and pressure of the reaction conditions of step (a), (c) heating the adiabatically expanded product mixture of step (b) with the exothermic heat from the reaction of the reactants reacting in step (a) by passing the heat to the adiabatically expanded product mixture and (d) transferring the heated adiabatically expanded product mixture of step (c) to the next processing step and repeating steps (a), (b), (c), and (d) under conditions whereby a continuous process results.

In another embodiment of the invention, the product mixture of step (a) is reacted with another reactant so as to form a final product mixture (step e), and steps (b), (c), and (d) are performed upon the final product mixture of step (e), and repeating steps (a), (e), (b), (c), and (d) under conditions whereby a continuous process results.

In another embodiment of the invention, steps (b) and (c) result in separation of one or more components.

The process is especially adopted for the carbonylation of $\alpha$-olefins up to six carbon atoms, especially propylene with an acid, such as an aqueous hydrogen fluoride solution of more than eighty (80) weight percent hydrogen fluoride, to form the corresponding carboxylic acid. Preferably the carbonylation with CO and $\alpha$-olefin uses a substantially anhydrous acid of hydrogen chloride or hydrogen fluoride, especially hydrogen fluoride, with carbon monoxide to form an acylium anion product, e.g., isobutyryl fluoride, which is separated from the product mixture. The process described herein is also adapted for the formation of the acylium anion product and its reaction with a hydroxy compound, preferably with less than the total amount of hydroxy compound required for reaction with substantially all of the acylium anion product of water or an alcohol of up to six carbon atoms, preferably methanol, ethanol, tertiary butanol or 2-ethyl hexanol, but especially methanol, to form an acid such as isobutyric acid or an ester such as methyl isobutyrate, and its separation from the product mixture. Examples of $\alpha$-olefins are ethylene; propylene; 1-butene; isobutene; 1-pentene; 2-methyl-1-butene; 3-methyl-1-pentene; 2,2-dimethyl propene; 1-hexene; 2methyl-1-pentene; 3-methyl-1-pentene; 4-methyl-1pentene; 2-ethyl-1-butene; 2,3-dimethyl-1-butene; or 3,3-dimethyl-1-butene. Examples of the acylium anion product are isobutyryl fluoride, isobutyryl chloride, propyl fluoride, 2-methyl-hexyryl fluoride, etc.

b. General Description of the Apparatus for the Process Described Herein

An apparatus for conducting the process described herein comprises several means. There is a reactor-heating means for conducting an exothermic reaction of a reaction mixture at pressures of up to 10,000 psia and for heating the product mixture after adiabatic expansion, an adiabatic means for adiabatically expanding the reacted mixture, a first transferring means for transferring the reaction mixture after reaction has occurred to the adiabatic means. The first transferring means is connected to the reactor-heating means and the adiabatic means. There is a second transferring means for transferring the adiabatically expanded product mixture around the reactor-heating means. The second transferring means is connected to the adiabatic means and the reactor-heating means. There is a subsequent processing means and a third transferring means for transferring the heated adiabatically expanded product from the reactor-heating means to the subsequent processing means. The third transferring means is connected to the heating means and to the subsequent processing means. There is a reactant feed means connected to the reactor means. The means are connected relative to each other in such a way that reactants can react exothermically while a reacted mixture adiabatically expands and an adiabatically expanded reacted mixture is heated by the exothermic reaction heat.

c. Illustration of the Process and Apparatus

A reactor for the process described herein is illustrated by reference to the drawing.

The feed source (8) of carbon dioxide, carbon monoxide, α-olefin (e.g., propylene) and anhydrous acid (e.g., hydrogen fluoride) enter through the inlet end (10) (the reactant feed means) into the reactor tube (12) where they react to form a product, e.g., an acylium anion product, such as isobutyryl fluoride, and produce exothermic heat. The reactor tube (12) is within a vessel (14) which is enclosed by an outer shell (16). The reactor tube (12) and outer shell (16) comprises the reactor-heating means. The product mixture from the reactor tube (12) leaves through outlet section (18) having an outlet end (19) and passes through an adiabatic pressure release valve (20) (adiabatic means) and adiabatically expands (more than one adiabatic valve can be used, so that a series of adiabatic expansions occur) and passes through a first conduit (26) through the shell (16) into the volume (28) enclosed by the shell (16) and surrounding the tube (12) where the adiabatically expanded product (surrounding environment) is heated through contact with the surface of the reactor tube (12). Reactor tube (12) is of sufficient length to conduct one or more exothermic reactions therein and is arranged within the volume (28) enclosed by the outer shell (16) of the vessel for effective transfer of the reaction heat to the surrounding environment (the adiabatically expanded product mixture, e.g., $CO_2$, CO, HF, IBF, and propylene), the heat content of which becomes greater than it originally had. This is manifested in, for example, a phase change, e.g., separation of gaseous HF from the mixture. The heated adiabatically expanded product mixture or part of the mixture passes through a second conduit (30) connected to the outer shell (16) of the vessel (14) and to the next processing apparatus not shown, e.g., distillation column, condenser, reactor, etc.

The vessel (14) can also include a plurality of baffles (32) positioned within the enclosed volume (28) to insure efficient mixing and heating of the adiabatically expanded product mixture. It can also include a third conduit means, such as take off line (34) positioned for removing heavy products from the expanded product mixture. It can also include a second reactant feed means such as reactant feed line (38) for feeding another reactant, e.g., $H_2O$ or methanol, to the reacted mixture for further exothermic reaction to form the final reacted mixture.

The vessel (14) as shown schematically in the drawing can be a conventional shell and tube reactor, having baffles of the donut design or in place of baffles a standard gridwork, or loose fill packings. The adiabatic pressure release valve can be any pressure release valve modified, for example, by insulating to maintain substantially adiabatic expansion, e.g., retaining from 20 percent to 100 percent of the heat, preferably as much heat as possible.

EXAMPLE I

The following example will illustrate the process and apparatus described herein.

A reaction mixture comprised of one hundred (100) gram moles of propylene per hour, 110 moles of carbon monoxide per hour and 1,500 moles of anhydrous hydrogen fluoride per hour are fed into the reactor tube (12) of vessel (14) at 80° C. and 2,800 psia, along with minor components (e.g., high boiler polymers which do not interfere with the reaction present from recycle), react to produce 2,800 Kcal per hour, and approximately 95 gram moles of isobutyryl fluoride per hour, which further reacts with 94.9 gram moles/hour of methanol fed through feed line (38) to produce 94.9 moles/hour of methyl isobutyrate and more exothermic heat, approximately 1,000 Kcal/hour. This product mixture passes through the adiabatic pressure release valve (20), and adiabatically expands. The adiabatically expanded product mixture of $CO_2$, CO, HF, propylene, isobutyryl fluoride (IBF) and methyl isobutyrate (MIB) passes through a pressure release valve (not shown) and at 40 psia and a temperature of approximately 50° C. enters the volume (28) of vessel (14) where the mixture encounters the exothermic reaction heat from tube (12). The $HF/CO/CO_2$ rich vapor passes upward and through line (30). The heavier fractions of isobutyryl fluoride, and methyl isobutyrate are removed via take off (34) and are further distilled to separate out the methyl isobutyrate. The high boiler polymers are discarded and isobutyryl fluoride is recycled for further reaction.

While the invention has been described with reference to specific details of certain illustrative embodiments, it is not intended that it shall be limited thereby except insofar as such details appear in the accompanying claims.

I claim:

1. A continuous process for the carbonylation of α-olefin having up to six carbon atoms for the preparation of a carboxylic acid or ester thereof and for employing the exothermic heat of the reaction to heat the product mixture for subsequent separation of at least one component from the product mixture; which comprises:
   (a) reacting a mixture of carbon monoxide, α-olefin of up to six carbon atoms, and an acid selected from the group consisting of an aqueous hydrogen fluoride solution of more than 20 weight percent hydrogen fluoride, and a substantially anhydrous acid selected from the group consisting of hydrogen fluoride and hydrogen chloride under pressure and at a low temperature under conditions whereby a product mixture and exothermic heat at pressure up to 10,000 psia and at temperature below about 100° C.
   (b) reacting the product mixture of step (a) with a hydroxy-containing compound selected from the group consisting of water and an alcohol having up to six carbon atoms under conditions whereby additional exothermic heat is produced and a carboxylic acid is produced when the hydroxy compound is water and under conditions whereby an ester is produced when the hydroxy compound is an alcohol.

(c) adiabatically expanding the product mixture of step (a) to below the temperature and pressure of the reaction conditions of step (a), (d) heating the adiabatically expanded product mixture of step (b) with the exothermic heat from reaction of the mixture of the reactants reacting in step (a) by passing the heat to the adiabatically expanded product mixture, and (e) transferring the heated adiabatically expanded product mixture of step (c) to a separation processing step and repeating steps (a), (b), (c), (d), and (e) under conditions whereby a continuous process results.

2. The process as recited in claim 1, wherein the acid is an aqueous hydrogen fluoride solution of more than eighty weight percent hydrogen fluoride.

3. The process as recited in claim 1, wherein the acid is substantially anhydrous hydrogen fluoride.

4. A continuous process for the preparation of a carboxylic acid or ester thereof and for employing the exothermic heat of the reaction to heat the product mixture for subsequent separation of at least one component from the product mixture which comprises:

(a) reacting a mixture of carbon monoxide an α-olefin of up to six carbon atoms and a substantially anhydrous acid selected from the group consisting of hydrogen fluoride and hydrogen chloride under pressure and at a low temperature under conditions whereby a product mixture comprises an acylium anion product and exothermic heat at pressures up to 10,000 psia and at a temperature below about 100° C. forms;

(b) reacting the product mixture of step (a) with a hydroxy containing compound selected from the group consisting of water and an alcohol of up to six carbon atoms under conditions whereby additional exothermic heat is produced and a carboxylic acid is produced when the hydroxy compound is water and under conditions whereby an ester is produced when the hydroxy compound is an alcohol;

(c) adiabatically expanding the product mixture of step (b) to below the temperature and pressure of the reaction conditions of step (a);

(d) heating the adiabatically expanded product mixture of step (c) with the exothermic heat from the reaction of the mixture of the reactants reacting in step (a) by passing the heat to the adiabatically expanded product mixture; and (e) transferring the heated adiabatically expanded product mixture of step (d) to a separation processing step and repeating steps (a), (b), (c), (d), and (e) under conditions whereby a continuous process results.

5. The process as recited in claim 4, wherein the amount of hydroxy compound is less than the total amount required for reaction of substantially all of the acylium anion product.

6. The process as recited in claim 4, wherein the substantially anhydrous acid is hydrogen fluoride.

7. The process as recited in claim 5, wherein the substantially anhydrous acid is hydrogen fluoride.

8. The process as recited in claim 4, wherein the α-olefin is propylene.

9. The process as recited in claim 5, wherein the α-olefin is propylene.

10. The process as recited in claim 6, wherein the α-olefin is propylene.

11. The process as recited in claim 7, wherein the α-olefin is propylene.

12. The process as recited in claim 8, wherein the alcohol is selected from the group consisting of methanol, ethanol, tertiary butanol, and 2-ethylhexanol.

13. The process as recited in claim 9, wherein the alcohol is selected from the group consisting of methanol, ethanol, tertiary butanol, and 2-ethylhexanol.

14. The process as recited in claim 10, wherein the alcohol is selected from the group consisting of methanol, ethanol, tertiary butanol, and 2-ethylhexanol.

15. The process as recited in claim 11, wherein the alcohol is selected from the group consisting of methanol, ethanol, tertiary butanol, and 2-ethylhexanol.

16. The process as recited in claim 8, wherein the alcohol is methanol.

17. The process as recited in claim 9, wherein the alcohol is methanol.

18. The process as recited in claim 10, wherein the alcohol is methanol.

19. The process as recited in claim 11, wherein the alcohol is methanol.

* * * * *